United States Patent [19]

De Baun

[11] 3,943,775
[45] Mar. 16, 1976

[54] METHOD AND APPARATUS FOR PREDICTING THE EXPLOSIVENESS OF A VOLUME CONTAINING INERT GAS AND HYDROCARBON VAPORS WHEN MIXED WITH AIR

[75] Inventor: Bruce De Baun, San Francisco, Calif.

[73] Assignee: Chevron Research Company, San Francisco, Calif.

[22] Filed: Mar. 24, 1975

[21] Appl. No.: 561,569

Related U.S. Application Data

[63] Continuation-in-part of Ser. No. 461,178, April 15, 1974, abandoned.

[52] U.S. Cl............................ 73/432 R; 73/23; 137/1
[51] Int. Cl.² ........... G01N 27/00; B65D 87/48; B65D 87/52
[58] Field of Search .......... 73/23, 35, 432 R; 137/1, 137/15; 141/4

[56] References Cited
UNITED STATES PATENTS

| | | | |
|---|---|---|---|
| 2,404,993 | 7/1946 | Sullivan | 73/27 R X |
| 2,544,651 | 3/1951 | Boardman | 137/1 X |
| 2,989,969 | 6/1961 | Gascoin | 137/1 |

*Primary Examiner*—James J. Gill
*Attorney, Agent, or Firm*—R. L. Freeland, Jr.; R. T. Kloeppel

[57] ABSTRACT

A method is disclosed for changing the inert gaseous content of a volume including hydrocarbon vapors to air without producing an explosive mixture. First a sample is obtained from the volume and then mixed with air to form a gas mixture. During the mixing, the mixture is monitored for values including percentage in tenths of lower explosive limit and percentage of oxygen. Then the values are evaluated to see if the mixture forms an explosive mixture; and, if so, the volume is purged with an inert gas prior to ventilating the volume with air to remove the inert gaseous content including hydrocarbon vapors from the volume without producing an explosive mixture of the hydrocarbon vapors and air.

Apparatus is also disclosed for use with the method. A sampling hose is located in a gaseous sample volume of inert gas and hydrocarbon vapors. It is connected to a valve to regulate the flow of gas through it. A second valve is connected to a source of air. These valves are also connected to respective sides of a tee so that the sample volume and air begin to mix in it as the mixture passes to a catalytic combustion indicator. The indicator reads percent oxygen and the percent (as a decimal) of the lower explosive limit.

The results may be recorded graphically or may be displayed on digital means by using two analog-to-digital converters, a summer and a digital display. One converter emits a unit pulse series for each tenth of the lower explosive limit; the other emits a unit pulse series for each percent of oxygen. These pulses are added in the summer and displayed on a digital display.

15 Claims, 4 Drawing Figures

METHOD AND APPARATUS FOR PREDICTING THE EXPLOSIVENESS OF A VOLUME CONTAINING INERT GAS AND HYDROCARBON VAPORS WHEN MIXED WITH AIR

RELATED APPLICATION

This application is related to and is a continuation-in-part of applicant's copending application Ser. No. 461,178, filed Apr. 15, 1974, and captioned "Method of Predicting the Explosiveness of a Volume Containing Inert Gas and Hydrocarbon Vapors When Mixed with Air", now abandoned. The entire disclosure of this copending application is hereby incorporated by reference as though set forth at length.

BACKGROUND OF THE INVENTION

1. Field of the Invention

This invention relates to a method for changing the inert gaseous content of a volume containing hydrocarbon vapors to air without producing an explosive mixture. More specifically, the invention relates to changing the inert gaseous content of a discharged crude-oil tank containing inert gas including hydrocarbon vapors to air without producing an explosive mixture in the presence of air.

2. Description of the Prior Art

Ocean oil-transportation companies are very interested in finding procedures and systems which will reduce the risks of fires or explosions occurring aboard their vessels, particularly those related to fires or explosions in the cargo tanks. As a result, a number of inerting systems have been installed on VLCC's (very large crude carriers) to displace the non-liquid content of these cargo tanks as a safeguard. Although an inerted cargo tank cannot support a fire or an explosion, a difficulty may arise when an inerted tank is being ventilated with air, that is, gas-freed in order to replace the inert gas with outside air. This gas-freeing of a tank allows men to freely enter the tank to do repairs without being poisoned or asphyxiated, as well as eliminating the potentially explosive hydrocarbon vapors. It is noted that this same problem occurs in petroleum refineries and other places where hydrocarbon vapors and air may mix.

Inerted tanks contain too little oxygen to support combustion; though they may contain, either throughout their volume or in isolated pockets, high concentrations of hydrocarbon vapors. When such a tank is ventilated with air, the tank atmosphere or inert gaseous content including hydrocarbon vapors may reach a stage of dilution where the supplied air has provided enough oxygen to mix with the hydrocarbon vapors and produce a combustible mixture that will explode when exposed to a source of ignition.

The current practice to eliminate the possibility of a combustible mixture forming is to purge the tank with a predicted flow volume of inert gas for a prescribed time, for example two hours, which has been empirically demonstrated to produce relatively hydrocarbon vapor-free volumes. Yet, there are three drawbacks to this method: one is that the particular system may be different from its state when a previously "safe" purge time was determined since hydrocarbon vapors may be formed from the residue in the tank during purging; second, the operation wastes both inert gas and time, since generally purging is continued longer than needed; third, a situation may arise when the volume of inert gas that was delivered was less than predicted.

Another way to test inerted tanks of low oxygen content is to mix a sample from the tank with air by mechanical flow proportioning devices, such as rotameters and pumps, before testing. Though these devices result in reliable data, they are not portable.

Another device, called a "flow proportioning valve," is available that connects to portable gas analyzers, detectors or indicators consisting of interchangeable orifices of different sizes which fix the percentage of air mixed with a sample. Since presently available detectors need oxygen of 11 to 21% of the volume to function, they cannot operate without such a valve when they are used to measure a sample from an inerted tank which contains an oxygen volume of less than 11%. The flow proportioning valve, however, is sensitive to the resistance of the sample feed line; thus, air proportion varies as the feed line and orifices accumulate foreign matter or the feed line length increases. For example, for a given orifice setting, the percentage of air dilution can vary from 24% with 1/8 inch-diameter tube, 2 feet long, to 51% for a similar tube 4.5 foot long, to 69% for a tube 15 feet long. Further distortion of readings is due to possible leaks in the feed line and the positive pressure that must be maintained in the inert gaseous volume to prevent the entrance of outside air in the volume.

The present invention can eliminate or substantially reduce the error that may be introduced by currently available system.

SUMMARY OF THE INVENTION

Briefly, this invention comprises a method for changing the inert gaseous content of a volume containing a mixture of inert gas and hydrocarbon vapors to air without producing an explosive mixture of hydrocarbon vapors and air in the volume. The steps of the method in general are: obtaining an inert gaseous sample from the volume; mixing the sample with air to form a mixture; monitoring it for values including the percent of hydrocarbons of the minimum required for combustion and percentage of oxygen. These values will then be evaluated to determine if the content of the volume and the air can produce an explosive mixture during ventilation and, if so, the volume is purged with an inert gas such as flue gas or nitrogen prior to ventilating the volume with air. The present invention also includes the step of converting the monitored percentages to whole numbers and summing these numbers together.

If the sum is greater than 21, the volume must be purged with an inert gas until the sum of numbers is 21 or less, at which time the volume may be gas-freed, i.e., ventilated with air to remove the inert gas. By plotting the values which were monitored on a graph, a graphic display of the exact path, in relation to its lower explosive limit, that the inert gaseous content of the volume being measured will follow when mixed with air is possible.

Apparatus is also disclosed for use with the method. A sampling hose is located in a gaseous sample volume of inert gas and hydrocarbon vapors. It is connected to a valve to regulate the flow of gas through it. A second valve is connected to a source of air. These valves are also connected to respective sides of a tee so that the sample volume and air begin to mix in it as the mixture passes to a catalytic combustion indicator. The indicator reads percent oxygen and the percent (as a decimal) of the lower explosive limit.

The results may be recorded graphically or may be displayed on digital means by using two digital-to-analog converters, a summer and a digital display. One converter emits a unit pulse series for each tenth of the lower explosive limit; the other emits a unit pulse series for each percent of oxygen. These pulses are added in the summer and displayed on a digital display.

DESCRIPTION OF THE PREFERRED EMBODIMENTS

Figure 1:
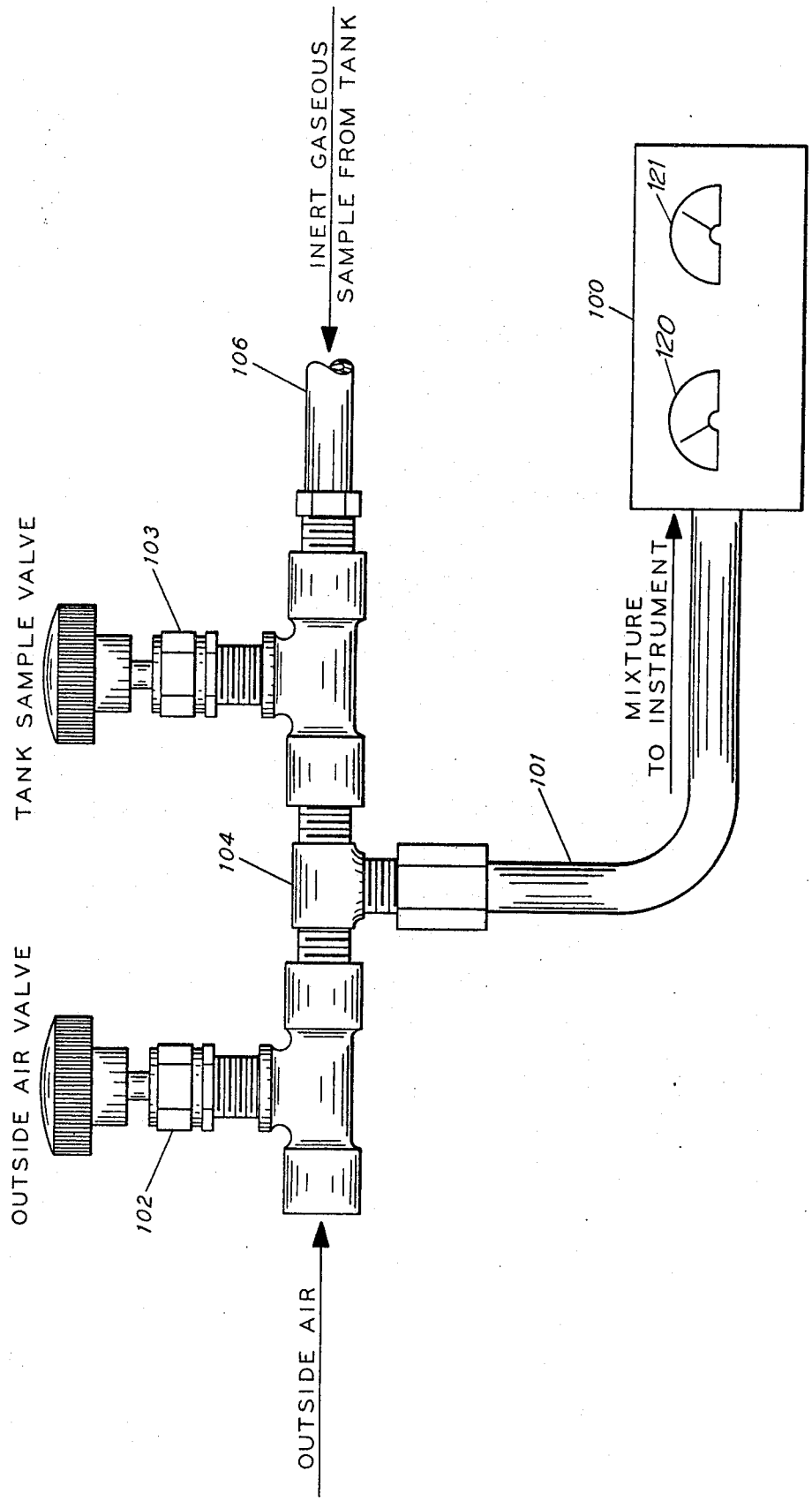
FIG. 1 illustrates apparatus assembled in accordance with the preferred embodiment of the present invention.

As indicated in FIG. 1, sampling hose 106 is connected at respective ends to both a volume or tank containing inerted gas and hydrocarbon vapors and tank sample valve 103. Connected to tee 104 is outside air valve 102, tank sample valve 103, and catalytic combustible indicator 100, such as a Bacharach-J.W., Model GPK, instrument, through conduit 101. Tank sample valve 103 and outside air valve 102 are stainless-steel needle valves which respectively control the flow of sample content and air to mix initially in tee 104 and throughout conduit 101.

Catalytic combustible indicator 100 is an instrument which includes a pump or other means for allowing only one-way flow through valves 102 and 103 and two meters. One meter 120 of indicator 100 measures the percentage of oxygen in a sample volume. The other meter 121 measures the fraction or percentage of the lower explosive limit (LEL) of a sample volume. (The LEL is the minimum quantity of hydrocarbon vapors needed to support combustion.) Meter 121 gives the LEL reading by comparing d.c. current flowing through a resistor including a platinum filament with hydrocarbon vapors oxidizing on its surface with a similar resistor that is isolated from it. Measurable current, however, occurs only when the hydrocarbon vapors are in the presence of sufficient oxygen, that is, 11 to 21% of the measured volume. This meter preferably gives readings as a decimal equivalent in tenths of LEL of the sample.

The operation in accordance with the present invention begins with the closing of mixing valves 102 and 103. Sampling hose 106 is inserted in the volume or tank to be tested prior to connecting hose 106 to tank sample valve 103. The positive pressure within the tank or a preattached sampling hose siphon causes the inert gaseous content of the tank to displace the outside air in hose 106. When all the outside air in hose 106 is displaced, the hose is connected to tank sample valve 103. At this time, indicator 100 is turned on, then outside air valve 102 is opened wide.

With air valve 102 wide open and tank sample valve 103 closed, the oxygen meter 120 of unit 100 will read approximately 21%. Tank sample valve 103 is then opened—preferably slowly enough so as not to lower the indicator meter reading of oxygen below 11% of the volume—until the other meter 121 of indicator 100 registers between 0.0 and 1.0 of the LEL (by definition 1.0 is the LEL of any given mixture) and the volume of oxygen registers between 11 and 21%. The tenths of LEL and percent oxygen of the sample are respectively read as values when both meters are steady and valves 102 and 103 are open. One can convert the values to whole numbers, and if these summed numbers are more than 21, the inert gaseous-air mixture will explode in the presence of a source of ignition. Further purging with inert gas is required until the summed values (after converting to whole numbers the tenths of LEL and percentages of oxygen) are 21 and less, at which time the tank mixture can be ventilated with air.

Figure 4:
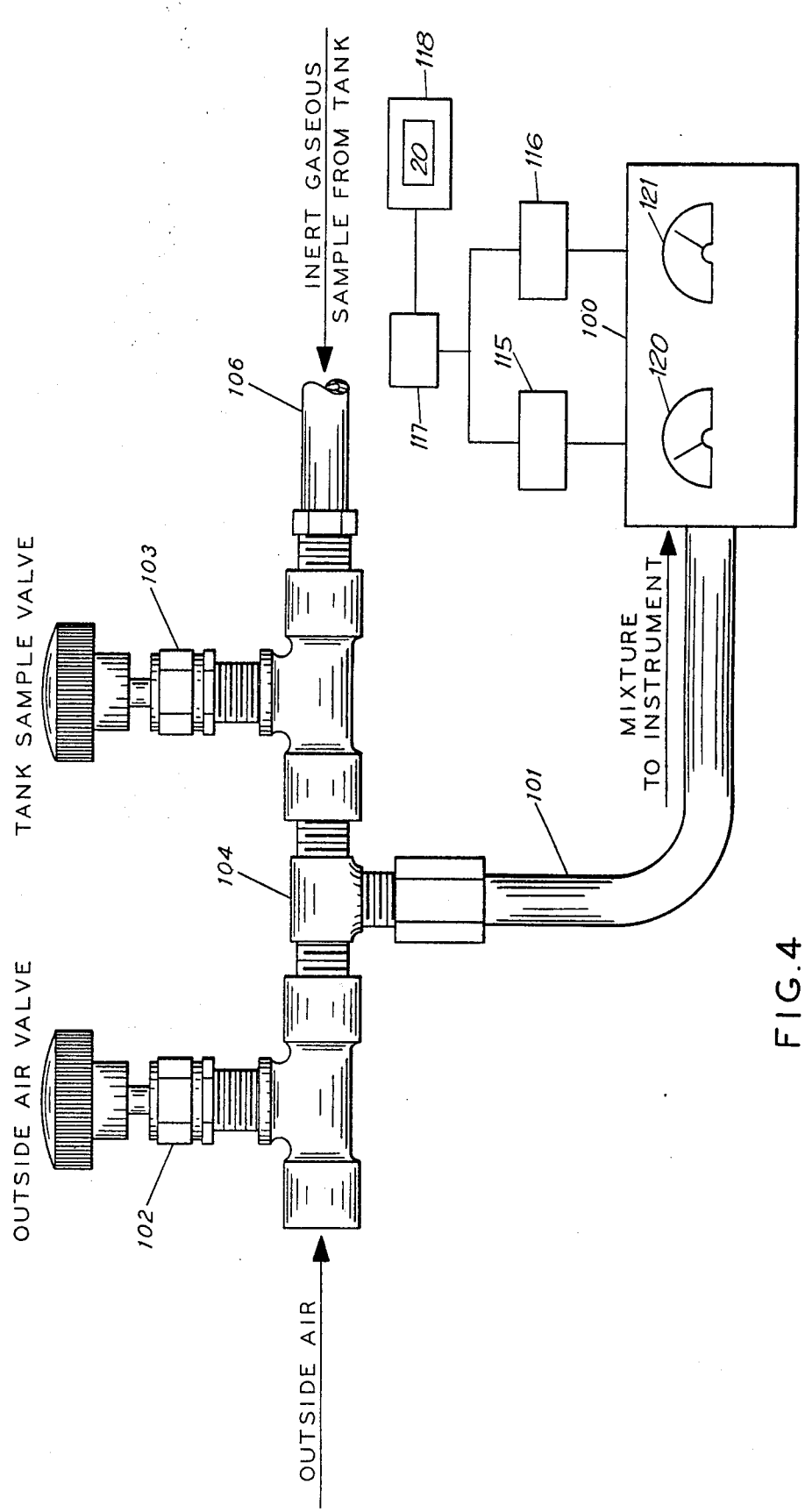
FIG. 4 illustrates the apparatus shown in FIG. 1 connected to analog-to-digital equipment which uses the method of the invention to display the results on a digital display.

The following describes a means for recording the sum of the whole numbers representing the fraction of LEL and percentage of oxygen (see FIG. 4). It comprises several digital and analog components: a first and a second analog-to-digital converter, 115 and 116, a summer 117, and a digital display 118. The first converter 115 is connected to oxygen meter 120 and emits an electric pulse or a unit pulse series for each percentage of oxygen in the sample. The second converter 116 is connected to catalytic combustion indicator 121 and emits a pulse or a unit pulse series for each fraction (in tenths) of LEL. Both pulses are fed to summer 117, which adds them. From here, they are displayed on a digital display 118, which has a reset switch (not illustrated) to clear and replace the display value when desired. The display digitally shows the sum, for example, in FIG. 4, the sum of 20 is displayed. In place of the display, a red light may be used to indicate a sum more than 21 and a green light if the sum is 21 or less.

Figure 3:
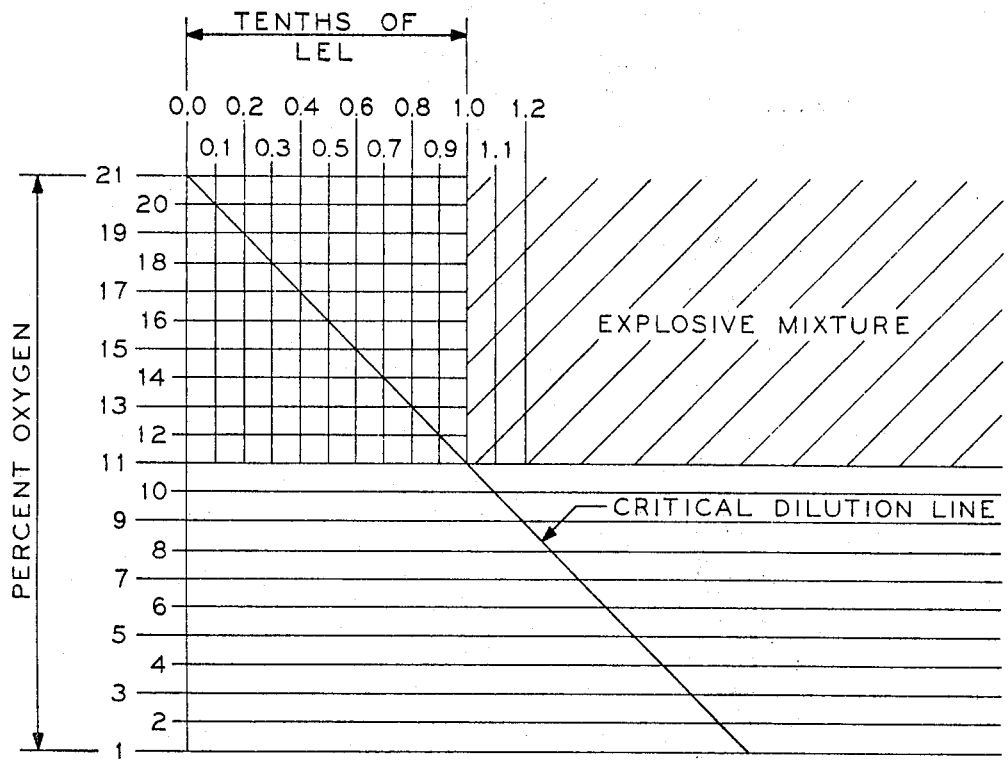
FIG. 3 is a second graph for conveniently illustrating the method of the present invention.
Figure 2:
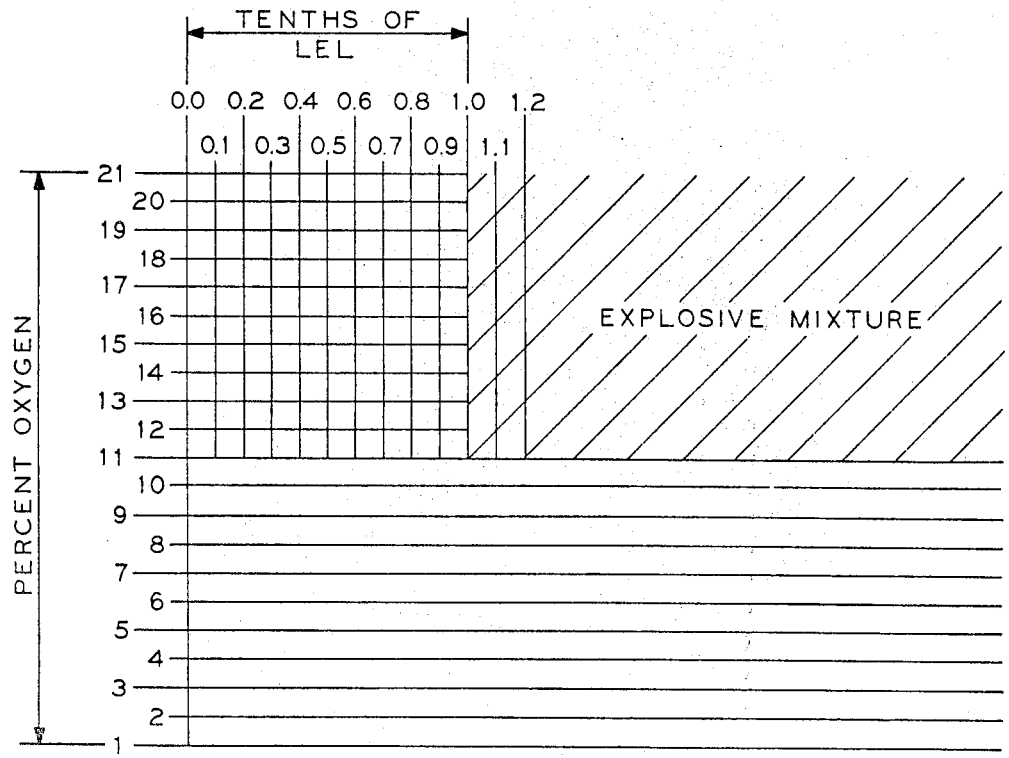
FIG. 2 is a graph for conveniently illustrating the method of the present invention.

On the other hand, one may use a graph (as a means for recording) such as one of those illustrated in FIGS. 2 and 3. Both graphically show the explosive range in diagonal lines. For example, the graph of FIG. 2 has the tenths as a deciminal equivalent of the fractions of LEL plotted along the x-axis and the whole number percentages of oxygen along the y-axis. Intersecting vertical lines defining the tenths of LEL of the volume are drawn through the lines corresponding to whole percentage values of oxygen on the graph.

A straight line can be drawn through the point representing coordinates of the two monitored values and a second point corresponding to a 0.0 lower explosive limit and an oxygen content of 21%. If this line crosses the 1.0 vertical LEL line, inert gas must be added to the volume. If the line does not intersect the vertical LEL line, the volume may be ventilated with air; during ventilation it is desirable that the volume be monitored as above to make sure that the volume does not generate additional hydrocarbon vapors that could produce an explosive mixture.

The second graph, illustrated in FIG. 3, is similar to the first graph; however, it has a critical dilution line plotted on the graph. This line sets the standard whether or not a tank containing hydrocarbon vapors and air will produce an explosive mixture. The critical dilution line is a straight line passing through a point whose coordinates are 0.0 LEL and 21% oxygen and a point whose coordinates are 1.0 LEL and 11% oxygen. If the point corresponding to the readings of tenths of LEL and percent oxygen of the volume is on or below the critical dilution line, then the tank or volume may be ventilated so as to gas-free the tank or volume without producing an explosive mixture. If, however, the point is above the critical dilution line, further purging with inert gas is required until the readings when plotted will give a point on or below the critical dilution line.

Further, the accuracy of this method using either of the two graphs may be checked by varying the sample entering indicator 100 so that a different set of coordinates can be plotted on the graph. The sample is varied by further opening or closing, but not completely, tank sample valve 103. (This will change both the oxygen meter and the LEL meter readings.) The method has been correctly conducted and indicator 100 is proven to be accurate if the plotted coordinates of the new values are on the straight line previously drawn with the prior values described above. This accuracy check is consistent with the fact that the plotted values are a graphic display of the exact path that the sample and the volume being measured take when mixed with air; such a feature is not available with currently used methods.

To safely carry out ventilation of a tank even after its monitored values indicate the tank may be safely ventilated, it is emphasized that it is necessary to monitor the tank by taking new values while it is being ventilated. This is prudent because hydrocarbon vapors may continue to form even during the ventilation process, making it feasible that an explosive mixture may be produced. If it does become apparent that an explosive mixture is possible, the ventilation process is stopped and purging is begun again until a point is reached where ventilation can safely be resumed. In short, the method described above is repeated.

By following the procedure described, the time expended in conducting purging operations is minimized, since the present invention allows one to predict precisely when purging can stop. For the same reason, the expense of inert gas such as nitrogen, which may not be readily available, is minimized. Furthermore, reading distortion due to feed line length, leaks or foreign matter in the valves or the feed line is nonexistent because this method measures the amount of oxygen that actually reaches the detecting device and not an assumed exact proportion. Most importantly, the present invention and indicator used with it are readily checked for accuracy by merely taking new values of the sample and plotting them as noted above.

The terms and expressions used in the preceding are terms of description and not of limitation; there is no intention in the use of the terms and expressions to exclude any equivalents of the features shown and described which are feasible within the scope of the following claims.

What is claimed is:

1. A method of changing the inert gaseous content of a volume containing an inert gas mixture including hydrocarbon vapors to air without producing an explosive mixture of hydrocarbon vapors and air in said volume, comprising:
   obtaining a sample of inert gas including hydrocarbon vapors from a volume having an inert gaseous content including hydrocarbon vapors;
   mixing said sample with air to form a mixture;
   monitoring said mixture as it is being mixed for values including tenths of lower explosive limit and percentage of oxygen;
   determining from said values if said gaseous content of said volume and air can form an explosive mixture and, if so, purging said volume with inert gas prior to ventilating said volume with air to displace the inert gas from said volume without producing an explosive mixture of hydrocarbon vapors and air.

2. The method of claim 1 further characterized by converting said values to whole numbers and, if the summed said whole numbers exceed 21, purging said volume with an inert gas; monitoring said volume until the summed whole numbers are 21 and less; and ventilating said volume with air to displace the inert gas from said volume when the summed whole numbers are 21 and less.

3. The method of claim 1 further characterized by monitoring said volume while said volume is being ventilated with air for new values including tenths of lower explosive limit and percentage of oxygen; determining from said new values if said gaseous content of said volume and air can form an explosive mixture; if so, purging said volume with inert gas prior to ventilating said volume with air to displace the inert gas from said volume.

4. A method of changing the inert gaseous content of a volume containing an inert gas mixture including hydrocarbon vapors to air without producing an explosive mixture of hydrocarbon vapors and air in said volume, comprising:
   obtaining a sample of inert gas including hydrocarbon vapors from a volume having an inert gaseous content including hydrocarbon vapors;
   mixing said sample with air to form a mixture;
   monitoring said mixture as it is being mixed for values including tenths of lower explosive limit and percentage of oxygen;
   providing a graph having the tenths of the lower explosive limit of the volume plotted along one edge of the graph and the percent oxygen of the volume along another edge of the graph;
   finding the point on the graph which corresponds with coordinates representing the values of tenths of lower explosive limit and percent oxygen of said volume; and
   adding inert gas to said volume for a period of time if the point is above the critical dilution line prior to ventilating said volume with air to remove the inert gas from said volume without producing an explosive mixture of hydrocarbon vapors and air.

5. The method of claim 4 further characterized by monitoring said volume while said volume is being ventilated with air for new values including tenths of lower explosive limit and percentage of oxygen;
   finding a point on the graph which corresponds with coordinates representing said new values;
   finding a point on the graph representing 0.0 lower explosive limit and 21% oxygen;
   drawing a straight line through each of said points;
   determining if said line crosses a vertical line representing the lower explosive limit of said volume; and
   adding inert gas to said volume for a period of time if the point is above the critical dilution line prior to ventilating said volume with air to remove the inert gas from said volume without producing an explosive mixture of hydrocarbon vapors and air.

6. The method of claim 4 further characterized by varying the sample being monitored;
   monitoring said varied sample for new values;

finding a new point on the graph which corresponds with coordinates representing said new values; and determining if said new point is on the straight line previously drawn.

7. A method of changing the inert gaseous content of a volume containing an inert gas mixture including hydrocarbon vapors to air without producing an explosive mixture of hydrocarbon vapors and air in said volume, comprising:

obtaining a sample of inert gas including hydrocarbon vapors from a volume having an inert gaseous content including hydrocarbon vapors;

mixing said sample with air to form a mixture;

monitoring said mixture as it is being mixed for values including tenths of lower explosive limit and percentage of oxygen;

providing a graph having the tenths of the lower explosive limit of the volume plotted along one edge of the graph and the percent oxygen of the volume along another edge of the graph;

finding a first point on the graph which corresponds with coordinates representing the values of the tenths of lower explosive limit and percent oxygen of said volume;

finding a second point on the graph representing 0.0 lower explosive limit and 21% oxygen;

drawing a straight line through said first point and said second point;

determining if said straight line crosses a vertical line representing the lower explosive limit of said volume;

adding inert gas to said volume, and if said straight line intersects said vertical line prior to ventilating said volume with air to remove the inert gas from said volume without producing an explosive mixture of hydrocarbon vapors and air.

8. The method of claim 7 further characterized by monitoring said volume while said volume is being ventilated with air for new values including tenths of lower explosive limit and percentage of oxygen;

finding a first point on the graph which corresponds to coordinates representing said new values;

finding a second point on the graph representing 0.0 lower explosive limit and 21% oxygen.

drawing a straight line through said first point and said second point;

determining if said line crosses a vertical line representing the lower explosive limit of said volume; and adding inert gas to said volume if said straight line intersects said vertical line prior to ventilating said volume with air to remove the inert gas from said volume.

9. The method of claim 7 further characterized by varying the sample being monitored;

monitoring said varied sample for new values;

finding a new point on the graph which corresponds with coordinates representing said new values; and determining if said new point is on the straight line previously drawn.

10. Apparatus for predicting the potential explosiveness of a gaseous volume containing inert gas and hydrocarbon vapors when air is added or substituted for said inert gas in said volume, comprising:

means for obtaining a gaseous sample of said inert gas and hydrocarbon vapors;

means for mixing said sample with air to form a resultant mixture thereof;

means for measuring the fraction of the lower explosive limit of the hydrocarbon vapors in said resultant mixture, said lower explosive limit being the unit minimum quantity of hydrocarbon vapors in a gas needed to support combustion;

means for separately measuring the percentage of oxygen in said resultant mixture; and means for summing said measurements of said fraction of the lower explosive limit and the percentage of oxygen, said sum being an indication of the explosiveness of said inert gas and hydrocarbon vapors when mixed with air.

11. The apparatus of claim 10 wherein said means for summing comprises:

a first analog-to-digital converter connected to said means for separately measuring the percentage of oxygen so that said first analog-to-digital converter emits a unit pulse series for each percentage of oxygen;

a second analog-to-digital converter connected to said means for measuring the fraction of the lower explosive limit of the hydrocarbon vapors so that said second analog-to-digital converter emits a unit pulse series for each fraction in tenths of the lower explosive limit;

a summer connected to said first and second converters to add the unit pulse series of each to form a sum; and a digital display connected to said summer to display said sum.

12. The apparatus of claim 10 wherein said means for determining said sum comprises a graph having two axes wherein the percentage of oxygen is plotted along one axis and said fraction of the lower explosive limit is plotted along the other axis;

said graph having a first line defining the lower explosive limit, said first line being straight and passing through a first point corresponding to 11% oxygen and the lower explosive limit, denoted as 1.0, and a second point corresponding to 21% oxygen and said lower explosive limit on said graph;

whereby on said graph a second straight line is drawn through a first point whose coordinates represent the measured fraction of the lower explosive limit and the measured percentage of oxygen and a second point whose coordinates are 0.0 as the fraction of the lower explosive limit and an oxygen content of 21%;

so that if said second line crosses the first line, more inert gas must be added to the volume, and if said second line does not intersect said first line, the volume may be vented with air.

13. The apparatus of claim 10 wherein said means comprises a graph having two axes whereon the fraction of the lower explosive limit is plotted as a decimal equivalent along one axis and the percentage of oxygen is plotted along the other axis;

said graph having a critical dilution line constructed thereon, said line being a straight line passing through a point whose coordinates are 0.0 fraction of the lower explosive limit and 21% oxygen and a second point whose coordinates are the lower explosive limit, denoted as 1.0, and 11% oxygen;

so that if a point corresponding to the readings of the fraction of lower explosive limit and percent oxygen of the mixture is on or below the critical dilution line, the volume from which said sample is obtained may be ventilated so as to gas-free the volume without producing an explosive mixture;
and if the point is above the critical dilution line, said volume is purged with inert gas until a subsequent point whose coordinates correspond to subsequent monitored readings of the fraction of lower explosive limit and percent oxygen of said volume is on or below the critical dilution line.

14. Apparatus for predicting the explosiveness of a volume containing inert gas and hydrocarbon vapor when mixed with air, comprising:
- a sampling hose having one end locatable in a gaseous volume containing a mixture of inert gas and hydrocarbon vapors to which it is desirable to add air;
- at least a pair of valve means, one of said valve means being connectable to the other end of said sampling hose to regulate the flow of said gaseous mixture through said hose, the other valve means being connectable to a source of air to regulate the flow of oxygen therethrough;
- a tee having three innerjoined passages wherein the two passages are respectively connected to each of said pair of valve means;
- a catalytic combustion indicator having its inlet connected to the third passage of said tee so that a selectively combinable sample of said gaseous mixture and air may be regulated by said valves to flow to said indicator, said indicator including means to measure the fraction of the lower explosive limit and the percentage oxygen of the combined sample; and
- means for recording the sum of said measurements as an indication of the explosiveness of said volume containing said mixture of inert gas and hydrocarbon vapors if air were added to said volume.

15. The apparatus of claim 14 wherein said means for recording the sum comprises:
- a first analog-to-digital converter connected to said means for separately measuring the percentage of oxygen so that said first analog-to-digital converter emits a unit pulse series for each percentage of oxygen;
- a second analog-to-digital converter connected to said means for measuring the fraction of the lower explosive limit of the hydrocarbon vapors so that said second analog-to-digital converter emits a unit pulse series for each fraction in tenths of the lower explosive limit;
- a summer connected to said first and second converters to add the unit pulse series of each to form a sum; and
- a digital display connected to said summer to display said sum.

* * * * *